United States Patent [19]
Benson et al.

[11] Patent Number: 5,258,496
[45] Date of Patent: Nov. 2, 1993

[54] ISOLATION AND PURIFICATION OF LUNG SURFACTANT PROTEIN

[75] Inventors: Bradley J. Benson, San Francisco; Douglas Buckley, Woodside; David Lesikar, Menlo Park; Asha Naidu, Mountain View; Kate B. Silverness, Castro Valley, all of Calif.

[73] Assignee: Scios Nova Inc., Mountain View, Calif.

[21] Appl. No.: 551,524

[22] Filed: Jul. 10, 1990

[51] Int. Cl.$^5$ .............................. C07K 3/12; C07K 3/20; C07K 15/06; C07K 15/16

[52] U.S. Cl. .................................. 530/350; 435/69.1; 435/69.7; 530/359; 530/416; 530/417; 530/424; 530/848

[58] Field of Search ............... 530/350, 848, 412, 416, 530/417, 418, 422, 424, 427, 359; 435/69.1, 71.2, 69.7

[56] References Cited

U.S. PATENT DOCUMENTS 4,882,422  11/1989  Taevsch et al. .................... 530/350

FOREIGN PATENT DOCUMENTS 0233044   8/1987   European Pat. Off. .
02037     4/1987   PCT Int'l Appl. .
06943    11/1987   PCT Int'l Appl. .
05820     8/1988   PCT Int'l Appl. .
08849    11/1988   PCT Int'l Appl. .
08850    11/1988   PCT Int'l Appl. .
8904362   5/1989   PCT Int'l Appl. .
00898     2/1990   World Int. Prop. O. .

OTHER PUBLICATIONS

Scarin et al., J. Lipid Research, vol. 30, No. 4, pp. 607-11, Apr. 1989.
Haagsman et al., Am. J. Physiol., vol. 257 No. 6, Part 1, pp. 6421-6429 (1989).
Phizackerley et al., Biochem J. 183:731-736 (1979).
Tanaka et al., Chem. Pharm. Bull. 31 (11):4091-4099 (1983).
Tanaka et al., Chem. Pharm. Bull. 31(11):4100-4109 (1983).
Tanaka et al., Journal of Lipid Research 27:475-485 (1986).
Whitsett et al., Pediatric Research 20(5):460-466 (1986).
Whitsett et al., Pediatric Research 20(8):744-749 (1986).

Primary Examiner—Jeffrey E. Russel
Attorney, Agent, or Firm—Morrison & Foerster

[57] ABSTRACT

Methods are provided for the isolation and purification of recombinant lung surfactant protein. The methods involve a multistep procedure including extraction with a $C_1$-$C_4$ aliphatic alcohol and chromatographic purification steps which employ a $C_1$-$C_4$ aliphatic alcohol as eluant. Purified proteins obtained using the disclosed isolation and purification steps are provided as well.

34 Claims, No Drawings

ISOLATION AND PURIFICATION OF LUNG SURFACTANT PROTEIN

TECHNICAL FIELD

This invention relates to lung surfactant proteins, and more particularly relates to novel methods for the isolation and purification thereof.

BACKGROUND OF THE INVENTION

Respiratory distress syndrome (RDS), also known as hyaline membrane disease, is a major cause of morbidity and mortality of the prematurely born infant. RDS is believed to be caused primarily by a deficiency of lung surfactant—a lipid-protein mixture which coats the airspaces of the lung—thereby reducing surface tension and preventing airspace collapse. The principal component of lung surfactant—dipalmitoylphosphatidylcholine (DPPC)—was identified several years ago (Klaus et al., *Proc Natl Acad Sci USA* (1961) 47:1858; Avery et al., *Am J Dis Child* (1959) 97:517). It is believed that administration of lung surfactant to an individual having or at risk of developing RDS is a desirable therapy, and the literature discloses various clinical studies of therapeutic administration of different lung surfactant preparations.

Mammalian lung surfactant is a complex material containing primarily phospholipids and associated proteins or apolipoproteins. The literature contains various lung surfactant protein preparations, including those with DPPC. Generally, these preparations include natural human surfactant (purified from human amniotic fluid—Merrit et al. *N End J Med* (1986) 315:787); semi-synthetic surfactant (prepared by combining DPPC and high-density lipoprotein—Halliday et al. *Lancet* (1984) 1:476); animal lung surfactant (isolated by organic extraction of the whole lung or lavage fluid—Kwong et al. *Pediatrics* (1985) 76:585); and purified human surfactant apoproteins (SP-A, SP-B, and/or SP-C purified from natural sources or derived by recombinant DNA technology—Jobe et al. *Am Rev Resp Dis* (1987) 136:1032, Glasser et al., *J Biol Chem* (1988) 263:10326, PCT Publication WO 88/05820, and PCT/US89/03417), and which may be reconstituted with surfactant lipids (Revak et al., *J Clin Invest* (1987) 81:826).

Significant progress has been made in the purification and characterization of the human surfactant apoproteins. However, different investigators have observed variation in the number of peptides with apparent molecular masses between 5 and 18 kDa, and their nominal molecular masses. Besides the molecular weight variations, researchers have experienced difficulty in separating the proteins isolated from native sources from their lipid components. Conventional lipid extraction procedures generally fail to separate the proteins completely from the surfactant lipids. One procedure which addresses this problem is described by Arjomaa and Hallman (*Ann Biochem* (1988) 171:207–212). That process involves a two-step purification of a human chloroform/methanol extract containing the SP4-6 peptide using a Sep Pak Florisil column, followed by reversed-phase high-pressure liquid chromatography (HPLC).

Recombinant production of surfactant proteins obviously does not require separation of protein from surfactant lipids. However, because microbially produced surfactant proteins can be expressed at a fairly high level, the high level of expression causes the recombinant protein to precipitate intracellularly in the form of refractile bodies, which do require further isolation and purification. The problem addressed by the present invention is how to safely and efficiently recover recombinant surfactant protein from the cell in a purified, renatured form that is acceptable for clinical use.

Solvent systems used both in the extraction of lung surfactant proteins and in subsequent chromatographic procedures typically involve combinations of non-polar solvents and buffers such as ether/ethanol, ether/chloroform, and chloroform/methanol. Many of these non-polar agents are quite toxic; for example, chloroform has been shown to be carcinogenic in rats. The use of such solvents in the purification of compounds and compositions intended for pharmaceutical applications therefore raises product safety concerns about potential toxicity in humans. It is, therefore, an object of the present invention to provide a process for isolating and purifying recombinant lung surfactant protein which avoids the use of chloroform-containing solvents and buffers. The use of substantially non-toxic solvents permits one to employ extraction and chromatographic procedures heretofore not used in the purification of surfactant proteins.

BACKGROUND ART

PCT Publication No. WO88/05820, inventors Schilling et al., entitled "Recombinant Alveolar Surfactant Protein" and of common assignment herewith, describes the complete coding sequences and amino acid sequences for canine and human 10K alveolar surfactant protein ("ASP"). The reference also describes clones encoding variants of both the higher and lower molecular weight forms of human ASP.

PCT Publication No. WO90/00898 describes a process for extracting a lipid and protein preparation from animal organs using a $C_1$–$C_{14}$ alkanol. The preparation may be used to treat respiratory distress syndrome.

PCT Publication No. WO87/02037, inventors Taeusch et al., describes the isolation and characterization of certain alveolar surfactant proteins.

PCT Publication No. WO87/06943, inventor Whitsett, describes methods of isolating an alveolar surfactant protein of 6,000 daltons and also describes the coadministration of the aforementioned protein with lipids for the treatment or prevention of surfactant deficiency syndrome.

Whitsett et al., *Pediatric Research* 20(5):460–466 (1986), describe the isolation and characterization of various surfactant-associated proteins. Whitsett et al., *Pediatric Research* 20(8):744–749 (1986), also relates to the surfactant-associated proteins and focuses specifically on the lower molecular weight, i.e., 6,000 dalton, protein.

PCT Publication Nos. WO88/08849 and WO88/08850 describe processes for recovering and purifying recombinant interleukin-2 (rIL-2) from transformed microorganisms using a sequence of solubilization and chromatographic procedures.

Tanaka et al., *Journal of Lipid Research* 27:475–485 (1986), present a study of compositions containing synthetic lung surfactant protein and mixtures of synthetic lipids.

Tanaka et al., *Chem Pharm Bull* 31(11):4091–4099 (1983), Tanaka et al., *Chem Pharm Bull* 31(11):4100–4109 (1983), and Phizackerley et al., *Bio-* chem J 183:731-736 (1979), all describe methods of isolating lung surfactant proteins which involve the use of chloroform as a solvent.

SUMMARY OF THE INVENTION

It is a primary object of the present invention to address the above-mentioned needs in the art and to provide a process for isolating and purifying recombinant lung surfactant SP-C (rSP-C) which avoids the use of highly toxic solvents.

It is another object of the invention to provide such a method for isolating and purifying rSP-C which involves an extraction step with a $C_1$-$C_4$ aliphatic alcohol or mixtures thereof.

It is still another object of the invention to provide such a process which involves separation of an SP-C fusion protein from a transformed microorganism, solubilization of inclusion bodies containing the fusion protein, cleavage of the fusion protein, precipitation of the rSP-C from the post-cleavage mixture, and extraction of the rSP-C using a $C_1$-$C_4$ aliphatic alcohol or mixtures thereof.

It is yet another object of the invention to provide such a process which further involves one or more chromatographic purification steps either instead of or following the extraction, wherein each of the chromatographic steps involves elution with a reagent composition that contains a $C_1$-$C_4$ aliphatic alcohol or mixtures thereof.

In a further aspect of the invention, chromatographic purification procedures are provided which separate rSP-C monomer from mixtures of lung surfactant proteins containing rSP-C monomer and rSP-C multimers.

It is still a further object of the invention to provide purified rSP-C obtained using the isolation and purification procedures described and claimed herein.

In one aspect of the invention, the process for isolating and purifying rSP-C from a transformed microorganism containing an expressed fusion protein of rSP-C, comprises the steps of:

(a) disrupting the cell membrane and cell wall of the microorganism to give a mixture of (i) cellular components and (ii) inclusion bodies containing the fusion protein;

(b) separating the inclusion bodies containing the fusion protein from the cellular components;

(c) solubilizing the inclusion bodies;

(d) treating the solubilized inclusion bodies with a cleavage reagent, thereby cleaving the fusion protein derived from the inclusion bodies to yield a cleavage mixture containing rSP-C;

(e) precipitating protein containing rSP-C from the cleavage mixture to provide a pellet that contains rSP-C; and (f) extracting the rSP-C from the pellet with an extraction reagent composition which comprises a $C_1$-$C_4$ aliphatic alcohol or an aqueous solution of a $C_1$-$C_4$ aliphatic alcohol.

In another aspect of the invention, step (f) in the just-described process is followed by one or more chromatographic purification steps. In a preferred embodiment, chromatographic purification involves hydrophobic interaction chromatography on a cyanopropyl column and/or a reversed-phase high-performance liquid chromatographic step. In both cases, the eluant used contains a $C_1$-$C_4$ aliphatic alcohol to specifically solubilize the rSP-C.

In still another aspect of the invention, the aforementioned procedures are used to purify rSP-B from a transformed microorganism containing an expressed fusion protein of rSP-B.

In still other aspects of the invention, purified proteins obtained using the aforementioned processes are provided, as are individual extraction and chromatographic purification methods.

DETAILED DESCRIPTION OF THE INVENTION

A. Definitions and overview:

As used herein, the term "rSP-C" refers to recombinant lung surfactant or lung surfactant-like polypeptides produced by a transformed microorganism and whose amino acid sequence is the same as, similar to, or substantially homologous to the native, relatively hydrophobic approximately 3-5 kd lung surfactant. Similarly, the term "rSP-B" refers to recombinant lung surfactant or lung surfactant-like polypeptides whose amino acid sequence is the same as, similar to, or substantially homologous to the native approximately 8 kd lung surfactant. Examples of such rSP-Bs and rSP-Cs are those described in PCT publications W088/05820 and W090/01540, of common assignment herewith. The disclosures of both these applications are incorporated herein by reference.

As used herein, the term "multimer" as applied to the rSP-C protein refers to dimers or larger aggregates of the rSP-C monomer.

Where "DTT" (dithiothreitol) is indicated as a preferred reagent in a variety of reagent compositions and procedures described herein, it will be appreciated by those skilled in the art that any number of alternative sulfhydryl reducing agent or agents could be used in its place.

The method of protein precipitation by water-miscible organic solvents has been employed since the early days of protein purification. Addition of an organic solvent to an aqueous extract containing proteins has a variety of effects which, in combination, can lead to protein precipitation. In general, the solvent used must be completely water-miscible, unreactive with proteins, and effective to precipitate the desired protein or proteins. Solvents that have been used to extract native mammalian surfactant proteins include such non-polar solvent systems as ether/ethanol, chloroform, chloroform/methanol in various ratios such as 3:1. While these solvent systems have proved effective for various extraction and/or chromatographic procedures, they are potential human carcinogens and thus present a risk, i.e., since using these solvents in purification procedures may result in some contamination of the final product.

As shown herein, it has been discovered that recombinant SP-C can be effectively solubilized with a number of lower aliphatic alcohols, employed either individually or in mixtures. Preferred alcohols comprise shorter carbon chains, as the longer-chain alcohols are more denaturing than short-chain ones and may also be less soluble in water. The $C_1$-$C_4$ aliphatic alcohols useful herein include methanol, ethanol, n-propanol, isopropanol, n-butanol, isobutanol, and t-butanol. (Where it is stated herein that a $C_1$-$C_4$ aliphatic alcohol may be used in extraction or chromatographic purification steps, it is to be understood that mixtures of such aliphatic alcohol may be used as well.)

B. Expression of the SP-C Fusion Protein:

The rSP-C is initially provided as a fusion protein expressed in bacterial cells. As is well-known, many eucaryotic proteins are incapable of being expressed in bacterial cells in any measurable yield, or, even if expressed in detectable quantities, are incapable of being expressed at commercially recoverable levels due to proteolysis of the foreign protein by the host. Small proteins such as SP-C appear to be especially sensitive to such degradation. As explained in copending, commonly assigned application Ser. No. 07/391,277, filed 8 Aug. 1989 abandoned, now continuing application Ser. No. 07/956,544 filed Oct. 2, 1992, pending and incorporated herein by reference (published through the PCT as WO 90/01540 on 22 Feb. 1990), proteins which are incapable of being expressed in high yield may be expressed as a fusion protein to increase the level of expression. For purposes of the present invention, it is preferred that the SP-C be expressed as a fusion protein with chloramphenicol acetyltransferase (CAT), which is known as a selectable marker and an easily assayed enzyme for the monitoring of efficiency of both eucaryotic and procaryotic expression (Delegeane, A. M., et al., *Molecular Cell Biology*, 7:3994–4002 (1987)).

The fusion proteins which one begins with in the isolation and purification methods of the present invention are substantially as described in the aforementioned patent application. The following is a brief summary of the fusion and expression process set forth in the aforementioned patent reference.

CAT encodes a 219 amino acid mature protein and the gene contains a number of convenient restriction endonuclease sites (5'-PvuII, EcoRI, DdeI, NcoI, and ScaI-3') throughout its length to test gene fusions for high level expression. These restriction sites may be used for ease of convenience in constructing hybrid gene sequences.

Expression constructs using CAT can employ most of the CAT-encoding gene sequence or a substantially truncated portion of the sequence encoding an N-terminal portion of the CAT protein linked to the gene encoding the desired heterologous polypeptide. These expression constructs, which demonstrate enhanced levels of expression for a variety of heterologous proteins, utilize a number of varying lengths of the CAT protein ranging in size from 73 to 210 amino acids. The 73 amino acid CAT fusion component is conveniently formed by digesting the CAT nucleotide sequence at the EcoRI restriction site. Similarly, the 210 amino acid CAT fusion component is formed by digesting the CAT nucleotide sequence with ScaI. These, as well as other CAT restriction fragments, may then be ligated to any nucleotide sequence encoding a desired protein to enhance expression of the desired protein.

The reading frame for translating the nucleotide sequence into a protein begins with a portion of the amino terminus of CAT, the length of which varies, continuing in-frame with or without a linker sequence into the SP-C sequence, and terminating at the carboxy terminus thereof. An enzymatic or chemical cleavage site may be introduced downstream of the CAT sequence to permit ultimate recovery of the cleaved product from the hybrid protein. Suitable cleavage sequences and preferred cleavage conditions will be described below.

To avoid internal cleavage within the CAT sequence, amino acid substitutions can be made using conventional site-specific mutagenesis techniques (Zoller, M. J., and Smith, M., *Nuc Acids Res* (1982) 10:6487–6500 and Adelman, J. P., et al., *DNA* (1983) 2:183–193). This is conducted using a synthetic oligonucleotide primer complementary to a single-stranded phage DNA to be mutagenized except for limited mismatching, representing the desired mutation. Of course, these substitutions would only be performed when expression of CAT is not significantly affected. Where there are internal cysteine residues, these may be replaced to help reduce multimerization through disulfide bridges.

Procaryotic systems may be used to express the CAT fusion sequence; procaryotic hosts are, of course, the most convenient for cloning procedures. Procaryotes most frequently are represented by various strains of *E. coli* (e.g., MC1061, DH1, RR1, W3110, MM294, B,C600hfl, K803, HB101, JA221, and JM101); however, other microbial strains may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar et al., *Gene* (1977) 2:95. pBR322 contains genes for ampicillin and tetracycline resistance, and thus provides multiple selectable markers which can be either retained or destroyed in construction of the desired vector.

In addition to the modifications described above which would facilitate cleavage and purification of the product polypeptide, the gene conferring tetracycline resistance may be restored to the exemplified CAT fusion vectors for an alternative method of plasmid selection and maintenance.

Although the *E. coli* tryptophan promoter-operator sequences are preferred, different control sequences can be substituted for the trp regulatory sequences. Commonly used procaryotic control sequences which are defined herein to include promoters for transcription initiation, optionally with an operator, along with ribosome binding site sequence, include such commonly used promoters as the beta-lactamase (penicillinase) and lactose (lac) promoter systems (Chang et al., Nature (1977) 198:1056), the lambda-derived $P_L$ promoter (Shimatake et al., Nature (1981) 292:128) and N-gene ribosome binding site, and the trp-lac (trc) promoter system (Amann and Brosius, Gene (1985) 40:183).

Transformed microorganisms producing the fusion protein are grown in a suitable growth medium containing compounds which fulfill the nutritional requirements of the microorganism. Growth media will typically contain assimilable sources of carbon and nitrogen, magnesium, potassium and sodium ions, and, optionally, amino acids, purine and pyrimidine bases, vitamins, minerals, and the like.

At the end of fermentation, the bacterial paste is collected by, e.g., cross-flow filtration, centrifugation, or other conventional methods. The concentrated paste is preferably stored at a temperature below about −50° C., preferably about −70° C., until further use.

C. Cell Disruption and Preparation of Inclusion Bodies:

Following concentration of the bacterial paste, the cell membranes and cell walls of the microorganisms are disrupted, either chemically, i.e., with alkali or with a compound such as 1-octanol, enzymatically, e.g., with lysozyme, or mechanically, i.e., using a commercially available homogenizer, as is well-known in the art. The end point of the disruption step can be monitored by microscopy and/or by adding a dye such as Coomassie Blue and monitoring its absorbance at 595 nm, which typically increases with cell lysis. Thai process step should be carried out for a time long enough to ensure that substantially all of the cells have been disrupted, and that substantially no intact cells will be carried through to subsequent process steps.

After cell disruption, the insoluble fraction of the whole-cell homogenate, containing inclusion bodies, is harvested by filtration, centrifugation, or the like. The inclusion body fraction is typically on the order of 10% of the initial wet-cell weight, and enrichment for the CAT/rSP-C fusion protein is thus desirable. To remove contaminating bacterial proteins, the inclusion body pellets are washed with a medium which contains 1M guanidine hydrochloride and a protein-solubilizing agent such as Triton x-100, together with dithiothreitol (DTT), ethylene diamine tetraacetic acid (EDTA), and buffering agents. After washing, the inclusion bodies are pelleted by centrifugation and washed again with the aforementioned medium. This washing procedure is important to achieve relatively high (50–70%) yields of rSP-C from the organic ($C_1$-$C_4$) aliphatic alcohol extraction step that follows later. This is due to the fact that this procedure, by washing away part of the contaminating bacterial protein, increases the proportion of inclusion body protein that is CAT-rSP-C fusion protein (to about 40%). When 1M guanidine.HCl is not included in the wash buffer, only about 25% of the inclusion body protein is CAT-rSP-C fusion, and the organic extraction yield falls to 20–30%. At this point, the inclusion bodies may, if desired, be frozen and stored.

Just prior to cleavage, the inclusion bodies are solubilized with a buffered medium containing on the order of 6M guanidine hydrochloride with DTT and EDTA, followed by high-speed centrifugation. By "high-speed centrifugation" is meant spinning the suspension in a centrifuge at about 8,000–40,000 x gravity (g), preferably about 10,000–20,000 x g, for a suitable time period, depending upon volume, generally about 10 minutes to 72 hours.

D. Cleavage of the Fusion Protein:

The reagent and methods used in cleaving the fusion proteins will depend, clearly, on the cleavage sequence incorporated into the fusion protein at the outset. Cleavage sequences which may be used herein include, for example, those which may be cleaved following methionine residues (cleavage reagent cyanogen bromide), glutamic acid residues (cleavage reagent endoproteinase Glu-C), tryptophan residues (cleavage reagent N-chlorosuccinimide with urea or with sodium dodecyl sulfate), and cleavage between asparagine and glycine residues (cleavage reagent hydroxylamine). For purposes of the present invention, cleavage with hydroxylamine is particularly preferred.

The inclusion bodies obtained in the previous step, in solubilized form, are treated with the selected cleavage reagent at ambient temperature. The reaction is allowed to proceed for as long as necessary to ensure substantially complete cleavage of the fusion protein.

E. Precipitation and Extraction of rSP-C:

After the cleavage reaction is complete, the reaction is stopped by dilution of the guanidine with buffered aqueous medium preferably containing a sulfhydryl reducing agent such as DTT (but not containing guanidine). This dilution causes precipitation of a proteinaceous mass which includes the rSP-C. The pellet or paste collected upon subsequent centrifugation is washed to remove extraneous matter and centrifuged again. At this point, the rSP-C is specifically dissolved via extraction with an extraction reagent composition which comprises a $C_1$-$C_4$ aliphatic alcohol or an aqueous solution of a $C_1$-$C_4$ aliphatic alcohol. As noted above, the inventors herein have now found that such a reagent composition specifically dissolves rSP-C while allowing the remaining proteins to remain in a precipitated state. (The discovery that a reagent composition containing a $C_1$-$C_4$ aliphatic alcohol is useful in specifically dissolving rSP-C was indeed surprising and unexpected in view of the fact that virtually all proteins are insoluble in lower alcohols.) Suitable $C_1$-$C_4$ aliphatic alcohols are as identified above in the section entitled "Definitions and Overview". Examples of preferred extraction reagent compositions include methanol, isopropanol, and aqueous solutions thereof. Examples of particularly preferred extraction reagent compositions include a 25% methanol/75% isopropanol mixture and aqueous solutions of 40%–100% isopropanol. Extraction may be repeated as necessary to increase the yield of rSP-C obtained.

It is preferred that the compositions disclosed herein as extraction reagents and eluants containing a $C_1$-$C_4$ aliphatic alcohol also contain about 0.001–100 mM acid, preferably a strong acid such as hydrochloric, trifluoroacetic, or phosphoric acid. This promotes the solubility of the protein.

F. Ion-Exchange:

Following extraction, ion-exchange chromatography may be performed in order to concentrate the rSP-C prior to size-exclusion chromatography. While any number of ion-exchange resins may be used in the initial chromatographic purification step, cation exchange resins such as sulfopropyl cellulose ("SP-cellulose"), sulfonated Sepharose, carboxymethyl ("CM") cellulose, CM Sephadex, CM Sepharose, CM silica, and Trisacryl are preferred. Strong cation exchange resins such as SP-cellulose or sulfonated Sepharose are more preferable, while an SP-cellulose column is particularly preferred. As with all of the chromatographic purification steps used in the present process, the eluant, like the extraction reagent composition, comprises a $C_1$-$C_4$ aliphatic alcohol, or gradients of aqueous solutions of a $C_1$-$C_4$ aliphatic alcohol.

In carrying out the ion-exchange step, the extract of the precipitated post-cleavage protein mixture, is equilibrated with the prepared resin, preferably at least 1 hour and more preferably overnight at room temperature. The rSP-C is then eluted (preferably on the order of about 6 hours at room temperature) with a reagent composition comprising a $C_1$-$C_4$ aliphatic alcohol, a buffer such as sodium acetate to increase pH and ionic strength, and a sulfhydryl reducing agent such as $\beta$-mercaptoethanol. The volume of the eluant is preferably much smaller than the volume of the extract, to effect marked concentration of the rSP-C. The eluted rSP-C may, if desired, be further concentrated by rotary or flash evaporation.

G. Size-Exclusion Chromatography:

A size-separation step is carried out either in addition to or instead of the aforementioned ion exchange step and is done using a sizing column, as is well known in the art. The rSP-C may be concentrated by rotary or flash evaporation. The concentrated rSP-C is loaded onto the selected sizing column, and equilibrated prior to use preferably with a $C_1$-$C_4$ aliphatic alcohol and 0.01–100 mM strong acid. A preferred resin for use in the sizing column is Sephadex LH60 prepared by hydroxypropylation of Sephadex G-50 (Pharmacia Fine Chemicals AB). Chromatography on such a column removes low molecular weight buffer components that are not desired in the final product, and assists in the separation of dimeric and aggregated rSP-C from the monomeric final product. When the column is run under preferred conditions, room temperature with a 75 cm long LH60 column, a pressure head of 60-65 cm, and an eluent reagent composition containing a lower aliphatic alcohol, as explained above, elution will occur after about 20 hours.

The preparation of rSP-C obtained from the sizing column is very pure, since rSP-C is soluble in the selected lower aliphatic alcohol while, as noted earlier, virtually no other peptides in the post-cleavage mixture are soluble under such extraction conditions.

H. Hydrophobic Interaction Chromatography Using a Cyanopropyl Column:

In another aspect of the invention, hydrophobic interaction chromatography is used to obtain pure rSP-C from a mixture of proteins, e.g., the entire post-cleavage protein mixture. Hydrophobic interaction chromatography can also be carried out following size exclusion to enhance the purity of the rSP-C obtained even further. The use of a cyanopropyl resin in such a step has proved to be unexpectedly superior relative to other purification methods. A suitable cyanopropyl resin may be obtained, for example, from Applied Biosystems (Foster City, Calif.). The cleavage mixture is preferably applied to the column in a buffered composition containing the $C_1$–$C_4$ aliphatic alcohol, guanidine hydrochloride, and dithiothreitol.

Development of the column is carried out with eluant compositions containing gradients of the $C_1$–$C_4$ aliphatic alcohol. Preferably, the column is run in the presence of low concentrations of acid, i.e., on the order of 0.001–100 mM of a preferably strong acid such as hydrochloric, phosphoric, or trifluoroacetic acid, or the like, as noted above with regard to extraction. Protein impurities elute early in the gradient while the rSP-C has been found to elute much later. The rSP-C obtained using this process has been confirmed to be extremely pure (typically >90%) by PAGE and by N-terminal sequencing. Western blot analysis also confirms these results.

I. Purification Using Reversed-Phase Resins:

In still another aspect of the invention, a method is provided for separating rSP-C monomer from rSP-C multimers. The use of reversed-phase HPLC for the separation of proteins is well-known; however, the resolution of protein or polypeptide mixtures on typical reversed-phase columns can be problematic. See, e.g., *Practical Protein Chemistry: A handbook*, Ed A. Darbre (New York: John Wiley & Sons, 1986), at page 189. The present method combines the discovery that rSP-C monomer is selectively soluble in $C_1$–$C_4$ aliphatic alcohols with the use of reversed-phase, purely "hydrophobic interaction", matrices or resins such as C4, C8, C18, and phenyl. The use of C4 and C8 columns in conjunction with an HPLC process is particularly useful here, i.e., in the separation of rSP-C monomer from rSP-C dimer in particular, since the dimer can remain associated with the monomer even after the preceding chromatographic steps have been carried out.

As with the cyanopropyl column, elution of rSP-C in the reversed-phase system is preferably accomplished using gradients with increasing quantities of the $C_1$–$C_4$ aliphatic alcohol. Again, a small quantity of strong acid is preferably present. Prior to loading the sample onto the reversed-phase column, the rSP-C obtained from the cyanopropyl column may be diluted with water or slightly acidic water. The diluted rSP-C may then be injected onto the reversed-phase column or dried, solubilized in a relatively high concentration of alcohol and diluted again in water or slightly acidic water. This procedure is believed to be the first that enables clean separation of the rSP-C monomer from the rSP-C dimer. The procedure may also be used on the post-cleavage cleavage mixture, but is more effective following the two chromatographic purification steps just described.

Hydrophobic interaction chromatography and reversed-phase chromatography may be carried out in either order. However, it is preferred that hydrophobic interaction chromatography be carried out first, followed by the reversed-phase column to insure optimum separation of the rSP-C monomer from the dimer. In other embodiments of the invention, one chromatographic purification step is used and not the other, e.g., where extremely pure rSP-C monomer is not required. In still other embodiments of the invention, the chromatographic procedures may be carried out directly following cleavage of the fusion protein, i.e., without precipitating or extracting the rSP-C.

J. Purification of RSP-B:

As noted above, "rSP-B" refers to recombinant lung surfactant or a lung surfactant-like polypeptide which is substantially similar to the native 8-10 kd lung surfactant protein. Both SP-B derived from the surfactant of bovine lungs and RSP-B isolated after bacterial expression have similar solubilities in $C_1$–$C_4$ alcohols such as isopropanol. In addition, the reversed-phase resins and specifically C4, C8, and phenyl, as well as large pore cyanopropyl resins, have been found to be useful in adsorbing SP-B. The elution characteristics for SP-B from these chromatographic supports are very similar to those described for SP-C. Thus, while the present method has been described in terms of its utility with rSP-C, it should also be useful in the isolation and purification of the lung surfactant protein known as rSP-B using the procedure described and claimed herein.

It is to be understood that while the invention has been described in conjunction with specific embodiments thereof, the foregoing description as well as the examples which follow are intended to illustrate and not limit the scope of the invention, which is defined by the appended claims. Other aspects, advantages and modifications within the scope of the invention will be apparent to those skilled in the art to which the invention pertains.

Experimental

Assay for Lung Surfactant Activity

In vitro methods have been devised to assess the ability of lung surfactant proteins to function by reducing surface tension (synonymous with increasing surface pressure) to generate a film on an aqueous/air interface. Studies using these methods have been performed on the isolated native 32K canine lung surfactant. (Benson et al., Prog Resp Res (1984) 18:83–92; Hagwood et al., Biochem (1985) 24:184–190).

Example 1

Production, Isolation and Purification of Recombinant SP-C

Expression: The mature form of human SP-C was expressed as a fusion protein with portions of the bacterial CAT protein. The surfactant protein was joined to the carboxy terminus of the CAT sequence through a hydroxylamine-sensitive asparagine-glycine linkage. The CAT-surfactant fusion was expressed from the tryptophan promoter of the bacterial expression vector pTrp233.

The plasmid was used to transform *E. coli* W3110 (ATCC accession no. 27325) and selected for ampicillin resistance. The transformants were grown in culture overnight at 37° C. in complete M9 medium containing M9 salts, 2 mM $MgSO_4$, 0.1 mM $CaCl_2$, 0.4% glucose, 0.5% amino acids, 40 µg/ml tryptophan, 2 µg/ml thiamine hydrochloride, and 100 µl/ml ampicillin sulfate.

Homogenization: At the end of fermentation, the bacterial paste (2 kg in wet cell weight) was collected by centrifugation and stored at −70° C. until use. The frozen paste was thawed at 4° C. overnight and resuspended in 5 liters per kg cells of 20 mM Tris-HCl buffer, pH 8, containing 10 mM EDTA and 1 mM DTT. A Tekmar high-shear mixer was used with a G-450 probe. The cell suspension was approximately 20% solids. After a uniform suspension was achieved, cells were disrupted by circulation through a Manton-Gaulin homogenizer equipped with a CD-30 valve at 15,000 psi. The suspension was recirculated, with stirring, for a time equivalent to four complete passes of the suspension volume through the homogenizer. Samples of homogenate were monitored for cell lysis by microscopy.

The undissolved fraction of the whole cell homogenate, containing inclusion bodies, was harvested by centrifugation at 5500 x g for 30 min at 4° C. The inclusion body fraction was about 10% of the initial wet cell weight. The inclusion body pellet was enriched for the CAT-rSP-C fusion protein by washing away contaminating bacterial proteins; the pellet was resuspended in buffer containing 1M guanidine.HCl, 20 mM Tris-HCl, pH 8, 10 mM EDTA, 1 mM DTT and 1% v/v Triton X-100 by stirring at 50-55% capacity with the Tekmar mixer at 4° C. After 15 min, the inclusion bodies were pelleted by centrifugation as before, and washed twice more with 10 volumes of buffer, i.e., 10 l per kg of inclusion body pellet. At this stage, inclusion body preparations were frozen and stored at about −70° C. (stable for months).

Inclusion Body Solubilization and Clarification: Washed inclusion bodies were thawed at 4° C. and solubilized with 10 volumes of buffer (i.e., 10 ml per g wet weight) containing 6M guanidine.HCl, 50 mM DTT, 50 mM EDTA, 20 mM Tris-HCl, pH 8, by stirring at 50-55% capacity at 4° C. for 30 min with the Tekmar mixer (G450 and G456 probes). The extract was clarified by centrifugation at 13,500 x g for 30 min at 4° C. The protein concentration of the extract was determined using the BCA (bicinchoninic acid) assay (bovine serum albumin as a standard), and then adjusted to 20 g/l.

Hydroxylamine Cleavage: CAT210/rSP-C fusion protein was cleaved with hydroxylamine. The cleavage reagent, freshly prepared immediately prior to use, was added to solubilized inclusion bodies at a 1:1 v/v ratio at ambient temperature. The reaction was allowed to proceed at 25° C. in a water bath for 48 hr.

Cleavage reagent was prepared as follows: Hydroxylamine ($NH_2OH \cdot HCl$), 140 g, was dissolved in 200 ml of 10.0M NAOH and 200 ml of 1.0M $K_2CO_3$. Solid guanidine.HCl (573 g) was added and the solution stirred until it returned to ambient temperature. The white precipitate that formed was removed by filtration through coarse scintered glass and 7.7 g of solid DTT were added with stirring. The pH was then adjusted to 10.0 using 10M NAOH and the volume brought to 1.0 l with pyrogen-free water. The buffer had a final concentration of 2M hydroxylamine, 0.2M $K_2CO_3$, 6M guanidine.HCl, 50 mM DTT.

Precipitation and Extraction: After 48 hr, the reaction was stopped by fivefold dilution with 4° C. 20 mM Tris-HCl, pH 8, containing 20 mM DTT. After incubation for 30 min at 4° C., precipitating protein was collected by centrifugation (15 min at 5500 x g), washed twice with 0.4 cleavage reaction volumes of the same buffer, centrifuged again and drained inverted at 0° C. for 30 min.

Extraction of the precipitate was performed into isopropanol, using half the volume used in the cleavage reaction. Extraction was performed under nitrogen for 1-2 hours at room temperature on a magnetic stirrer (the time can be varied depending on the scale of the extraction procedure). The supernatant was collected by centrifugation at 5900 Xg for 25 min. at 4° C. At this stage, the extract was stored overnight at −20° C.

Example 2

Chromatographic Purification

1. Ion Exchange: Sulfopropyl cellulose ("SP-cellulose") is used primarily to concentrate rSP-C prior to size-exclusion chromatography on LH60 resin. SP-cellulose may be prepared by standard methods and then equilibrated into methanol. It may then be equilibrated in buffer, e.g., "buffer A" (19:1 isopropanol:0.1N HCl, plus 50 mM β-mercaptoethanol and 0.01 volume NaAc, 2M, pH 4). The organic extract provided in Example 1, at room temperature, is then made 5 mM in HCl by addition of 1M solution. Resin is added batchwise and incubated overnight at room temperature with mixing. SP-cellulose is collected and washed 6x with buffer A. rSP-C may then be eluted overnight with a small volume (50 ml per liter of cleavage) of a buffer such as "buffer B" (buffer A plus 0.025 volumes of NaAc pH 6, 2M) and clarified by filtration through glass wool.

2. Size-Exclusion Chromatography: LH60 column chromatography removes dimeric and aggregated rSP-C, as well as undesired buffer components, from the monomeric final product. The column was packed with Sephadex LH60 obtained directly from Pharmacia. Running solvent was 95% isopropanol, 5% 0.1N HCl v/v. The column (75 cm in length) was run at room temperature; a pressure head of 60 cm and a flow rate of 4 ml/cm² per hour.

The volume of sample applied to the column was 3% of bed volume. Elution of monomeric rSP-C occurred after about 20 hours.

Example 3

Hydrophobic Interaction Chromatography Using a Cyanopropyl Column

This example describes the use of a cyanopropyl resin to obtain pure rSP-C from the entire post-cleavage protein mixture (i.e., without precipitation and extraction) using isopropanol:water solutions to elute the protein.

Isopropanol, guanidine hydrochloride and DTT were added to the post-cleavage mixture of Example 1 to give final concentrations of 35% isopropanol, 6M guanidine hydrochloride, and 50 mM DTT. This was applied to a cyanopropyl column (4.6 mm × 3 cm; resin obtained from Applied Biosystems, Foster City, Calif.). The column was then developed in 5 mM HCl with an isopropanol gradient from 35% to 95% at a flow rate of approximately 0.5 ml/min. Protein impurities eluted early in the gradient, while the rSP-C eluted much later, as determined by the UV absorbance at 228 nm. Western blot analysis confirmed these results. Substantially pure (>90%) rSP-C was thus obtained from the entire post-cleavage protein mixture.

Example 4

Reversed-Phase HPLC

In this example, the use of reversed-phase resins to separate, purify and assay for rSP-C is described. The method has been found to be useful for separating rSP-C monomer from a protein mixture which includes the rSP-C dimer.

A mixture of rSP-C monomer and dimer, approximately 95% pure, was obtained from the LH60 column of Example 2 in isopropanol:0.1N HCl (19:1). The sample was diluted with 1 part 5 mM HCl, injected directly onto a reversed-phase HPLC C8 column (Brownlee Cartridge, 2.1 mm × 3 cm). The column was developed in the presence of 5 mM HCl, with a 40-min gradient from 20%-90% isopropanol. The flow rate used was approximately 0.5 ml/min, and the eluted rSP-C monomer was detected via UV absorbance at 228 nm (Spectroflow 757 Detector). The chart recorder speed was 2 mm/min. Virtually complete separation of the monomer from the mixture containing the dimer was observed, as confirmed by UV and SDS-PAGE.

Example 5

The method of the preceding example was followed, except that prior to injection of the sample onto the HPLC column, the sample was dried in a Speed-Vac and dissolved in 95% isopropanol with 50 mM HCl and diluted with 50 mM HCl to give a final concentration of 50% isopropanol. Substantially the same results as in the preceding example were obtained, except that a somewhat cleaner background was obtained here.

Example 6

The method of Example 4 was used with a 25-min, 35%-75% gradient of the buffer solution described. Substantially the same results as in Example 5 were obtained.

Example 7

The method of Example 4 was used with a 40-min, 35%-95% gradient of the buffer solution described. Substantially the same results as in Example 5 were obtained.

Example 8

The procedure of Example 5 is repeated using a reversed-phase HPLC C4 column. Substantially the same results as set forth in Example 5 were obtained.

Example 9

The procedure of Example 5 was followed, except a reversed-phase HPLC phenyl column (4.6 mM × 3 cm, Applied Biosystems, Foster City, Calif.) was used. Substantially the same results as set forth in Example 5 were obtained.

We claim:

1. A process for isolating and purifying recombinant lung surfactant SP-C (rSP-C) from a transformed microorganism containing an expressed fusion protein of rSP-C, comprising the steps of:
   (a) disrupting the cell membrane and cell wall of the microorganism to give a mixture of (i) cellular components and (ii) inclusion bodies containing the fusion protein;
   (b) separating the inclusion bodies containing the fusion protein from the cellular components;
   (c) solubilizing the inclusion bodies;
   (d) treating the solubilized inclusion bodies with a cleavage reagent, thereby cleavage the fusion protein derived from the inclusion bodies, to yield a cleavage mixture containing rSP-C;
   (e) precipitating protein containing the rSP-C from the cleavage mixture to provide a pellet containing rSP-C; and
   (f) extracting the rSP-C from the pellet with an extraction reagent composition which consists essentially of one or more $C_1-C_4$ aliphatic alcohol or an aqueous solution thereof, said alcohol or aqueous solution optionally containing about 0.001–100 mM strong acid.

2. The process of claim 1, wherein the fusion protein is a CAT fusion protein.

3. The process of claim 1, further including, after step (b) and prior to step (c):
   (a') washing the inclusion bodies with a buffer effective to remove extraneous proteinaceous materials.

4. The process of claim 3, wherein the buffer contains Triton X-100 and guanidine.HCl.

5. The process of claim 1, wherein the solubilizing of step (c) is carried out with a solubilizing composition comprising aqueous guanidine hydrochloride.

6. The process of claim 5, wherein the guanidine hydrochloride is 5M to 7M.

7. The process of claim 6, wherein the guanidine hydrochloride is approximately 6M.

8. The process of claim 5, wherein the solubilizing composition further comprises a sulfhydryl reducing agent.

9. The process of claim 8, wherein the sulfhydryl reducing agent comprises dithiothreitol.

10. The process of claim 1, further including, after step (d) and prior to step (e):
    (d') diluting the cleavage mixture with a solvent containing a $C_1-C_4$ aliphatic alcohol optionally containing a sulfhydryl reducing agent.

11. The process of claim 10, further including, after step (d'), carrying out chromatographic purification of the diluted cleavage mixture using an eluant which comprises a $C_1-C_4$ aliphatic alcohol.

12. The process of claim 1, wherein the extraction reagent composition comprises isopropanol.

13. The process of claim 1, wherein the extraction reagent composition comprises methanol.

14. The process of claim 13, wherein the extraction reagent composition additionally comprises about 0.001 to 100 mM acid.

15. The process of claim 1, wherein the extraction reagent composition comprises an aqueous solution of 40% to 100% isopropanol.

16. The process of claim 15, wherein the extraction reagent composition additionally comprises about 0.001 to 100 mM acid.

17. The process of claim 1, further including, after step (f): (g) carrying out chromatographic purification on the extracted rSP-C pellet using an eluant which comprises a $C_1$–$C_4$ aliphatic alcohol.

18. The process of claim 17, wherein the chromatographic purification comprises ion-exchange chromatography.

19. The process of claim 18, wherein the eluant is an aqueous solution of isopropanol.

20. The process of claim 18, wherein the ion-exchange chromatography is carried out using a sulfopropyl cellulose column.

21. The process of claim 17, wherein the chromatographic purification comprises size-exclusion chromatography.

22. The process of claim 21, wherein the size-exclusion chromatography is carried out using an Sephadex LH-60 column.

23. The process of claim 17, wherein the chromatographic purification comprises: (a) ion-exchange chromatography, followed by (b) size-exclusion chromatography.

24. The process of claim 17, wherein the chromatographic purification comprises a hydrophobic interaction separation on a cyanopropyl column.

25. The process of claim 17, wherein the chromatographic purification comprises reversed-phase high-performance liquid chromatography using a C4 or C8 column.

26. The process of claim 17, wherein the chromatographic purification comprises: (a) hydrophobic interaction separation on a cyanopropyl column; and (b) reversed-phase high-performance liquid chromatography.

27. A process for isolating and purifying recombinant lung surfactant SP-C (rSP-C) from a transformed microorganism containing an expressed fusion protein of rSP-C, comprising the steps of:
 (a) disrupting the cell membrane and cell wall of the microorganism to give a mixture of (i) cellular components and (ii) inclusion bodies containing the fusion protein;
 (b) separating the solubilized bodies containing the fusion protein from the cellular components;
 (c) solubilizing the inclusion bodies;
 (d) treating the solubilized inclusion bodies with a cleavage reagent, thereby cleaving the fusion protein derived from the inclusion bodies, to yield a cleavage mixture containing rSP-C;
 (e) precipitating protein containing the rSP-C from the cleavage mixture to provide a pellet containing rSP-C;
 (f) extracting the rSP-C from the pellet with an extraction reagent composition which consists essentially of one or more $C_1$–$C_4$ aliphatic alcohol or an aqueous solution thereof, said alcohol or aqueous solution optionally containing about 0.001–100 mM strong acid; and
 (g) chromatographically purifying the extracted rSP-C using
 hydrophobic interaction chromatography using a cyanopropyl column;
 and using an eluant comprising a $C_1$–$C_4$ aliphatic alcohol.

28. A process for isolating and purifying recombinant lung surfactant SP-C (rSP-C) from a transformed microorganism containing an expressed fusion protein of rSP-C, comprising the steps of:
 (a) disrupting the cell membrane and cell wall of the microorganism to give a mixture of (i) cellular components and (ii) inclusion bodies containing the fusion protein;
 (b) separating the inclusion bodies containing the fusion protein from the cellular components;
 (c) solubilizing the inclusion bodies;
 (d) treating the solubilized inclusion bodies with a cleavage reagent, thereby cleaving the fusion protein derived from the inclusion bodies, to yield a cleavage mixture containing rSP-C; and carrying out either
 (e) hydrophobic interaction chromatographic purification on a cyanopropyl column; or
 (f) reversed-phase high performance liquid chromatographic purification; or
 carrying out both steps (e) and (f).

29. A process for isolating and purifying recombinant lung surfactant SP-C (rSP-C) from a transformed microorganism containing an expressed fusion protein of rSP-C, comprising the steps of:
 (a) disrupting the cell membrane and cell wall of the microorganism to give a mixture of (i) cellular components and (ii) inclusion bodies containing the fusion protein;
 (b) separating the solubilized bodies containing the fusion protein from the cellular components;
 (c) solubilizing the inclusion bodies;
 (d) treating the solubilized inclusion bodies with a cleavage reagent, thereby cleaving the fusion protein derived from the inclusion bodies, to yield a cleavage mixture containing rSP-C;
 (e) precipitating protein containing the rSP-C from the cleavage mixture to provide a pellet containing rSP-C;
 (f) extracting the rSP-C from the pellet with an extraction reagent composition which consists essentially of one or more $C_1$–$C_4$ aliphatic alcohol or an aqueous solution thereof, said alcohol or aqueous solution optionally containing about 0.001–100 mM strong acid; and
 (g) chromatographically purifying the extracted rSP-C using reversed-phase high-performance liquid chromatography using a column and using an eluant comprising a $C_1$–$C_4$ aliphatic alcohol.

30. The process of claim 29 wherein the column is a $C_4$ column.

31. The process of claim 29 wherein the column is a $C_8$ column.

32. The process of claim 29 wherein the column is a phenyl column.

33. A process for isolating and purifying recombinant lung surfactant SP-C (rSP-C) from a transformed microorganism containing an expressed fusion protein of rSP-C, comprising the steps of:
 (a) disrupting the cells membrane and cell wall of the microorganism to give a mixture of (i) cellular components and (ii) inclusion bodies containing the fusion protein;
 (b) separating the inclusion bodies containing the fusion protein from the cellular components;
 (c) solubilizing the inclusion bodies;

(d) treating the solubilized inclusion bodies with a cleavage reagent, thereby cleaving the fusion protein derived from the inclusion bodies, to yield a cleavage mixture containing rSP-C; and (e) carrying out reversed-phase high performance liquid chromatographic purification.

34. A process for isolating and purifying recombinant lung surfactant SP-C (rSP-C) from a transformed microorganism containing an expressed fusion protein of rSP-C, comprising the steps of:

(a) disrupting the cells membrane and cell wall of the microorganism to give a mixture of (i) cellular components and (ii) inclusion bodies containing the fusion protein;

(b) separating the inclusion bodies containing the fusion protein from the cellular components;

(c) solubilizing the inclusion bodies;

(d) treating the solubilized inclusion bodies with a cleavage reagent, thereby cleaving the fusion protein derived from the inclusion bodies, to yield a cleavage mixture containing rSP-C;

(e) carrying out hydrophobic interaction chromatographic purification on a cyanopropyl column; and (f) carrying out reversed-phase high performance liquid chromatographic purification.

* * * * *